US00PP26656P2

(12) United States Plant Patent
Kubala et al.

(10) Patent No.: US PP26,656 P2
(45) Date of Patent: Apr. 26, 2016

(54) ***BUXUS* PLANT NAMED 'GREJADE'**

(50) Latin Name: *Buxus microphylla*
Varietal Denomination: Grejade

(71) Applicants: Jane Marie Kubala, El Campo, TX (US); Bill Barr, Rosenberg, TX (US)

(72) Inventors: Jane Marie Kubala, El Campo, TX (US); Bill Barr, Rosenberg, TX (US)

(73) Assignee: Greenleaf Nusery Company, Park Hill, OK (US)

( * ) Notice: Subject to any disclaimer, the term of this patent is extended or adjusted under 35 U.S.C. 154(b) by 110 days.

(21) Appl. No.: 14/121,253

(22) Filed: Aug. 14, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Buxus microphylla*, 'Grejade', that is characterized by its very small, evergreen leaves, its compact, dense growth habit with leaves that have very short internode lengths, its moderate growth rate, and its cold hardiness to U.S.D.A Zone 5.

2 Drawing Sheets

Botanical classification: *Buxus microphylla.*
Variety denomination: 'Grejade'.

BACKGROUND OF THE INVENTION

The present invention relates to a new and distinct cultivar of *Buxus microphylla* and will be referred to hereafter by its cultivar name, 'Grejade'. 'Grejade' is a new cultivar of boxwood grown for use as a landscape shrub.

The new cultivar was discovered by one of the Inventors as a naturally occurring branch mutation of the cultivar 'Gregem' (U.S. Plant Pat. No. 21,159) growing in a container in a nursery in September of 2010 in El Campo, Tex.

Asexual propagation of the new cultivar was first accomplished by one of the Inventors using softwood stem cuttings in El Campo, Tex. in September of 2011. Asexual propagation of the new cultivar has determined that the characteristics are stable and are reproduced true to type in successive generations.

SUMMARY OF THE INVENTION

The following traits have been repeatedly observed and represent the characteristics of the new cultivar as grown outdoors in trial beds and in containers in El Campo, Tex. These attributes in combination distinguish 'Grejade' as a unique cultivar of *Buxus.*

1. 'Grejade' exhibits very small, evergreen leaves.
2. 'Grejade' exhibits a compact, dense growth habit with leaves that have very short internode lengths.
3. 'Grejade' exhibits a moderate growth rate.
4. 'Grejade' is hardy to U.S.D.A Zone 5.

'Grejade' can be most closely compared to 'Gregem', the parent plant. 'Gregem' is similar to 'Grejade' in having a dense and compact growth habit with small leaves, however 'Gregem' differs from 'Grejade' in having larger leaves with longer internodes (when grown under the same conditions), in having stems that are longer and quadrangular in shape, and in having a more vigorous growth rate (25 to 30% faster growth rate). 'Grejade' may also be compared to 'Wintergreen' (not patented). 'Wintergreen' differs from 'Grejade' in having larger leaves, a less dense growth habit and by maturing to a larger sized plant.

BRIEF DESCRIPTION OF THE DRAWING

The accompanying colored photographs illustrate the overall appearance and distinct characteristics of 3 year-old plants as grown outdoors in three-gallon containers in El Campo, Tex.

The photograph in FIG. 1 is a side view and illustrates the overall plant habit and appearance of 'Grejade'.

Figure 1:
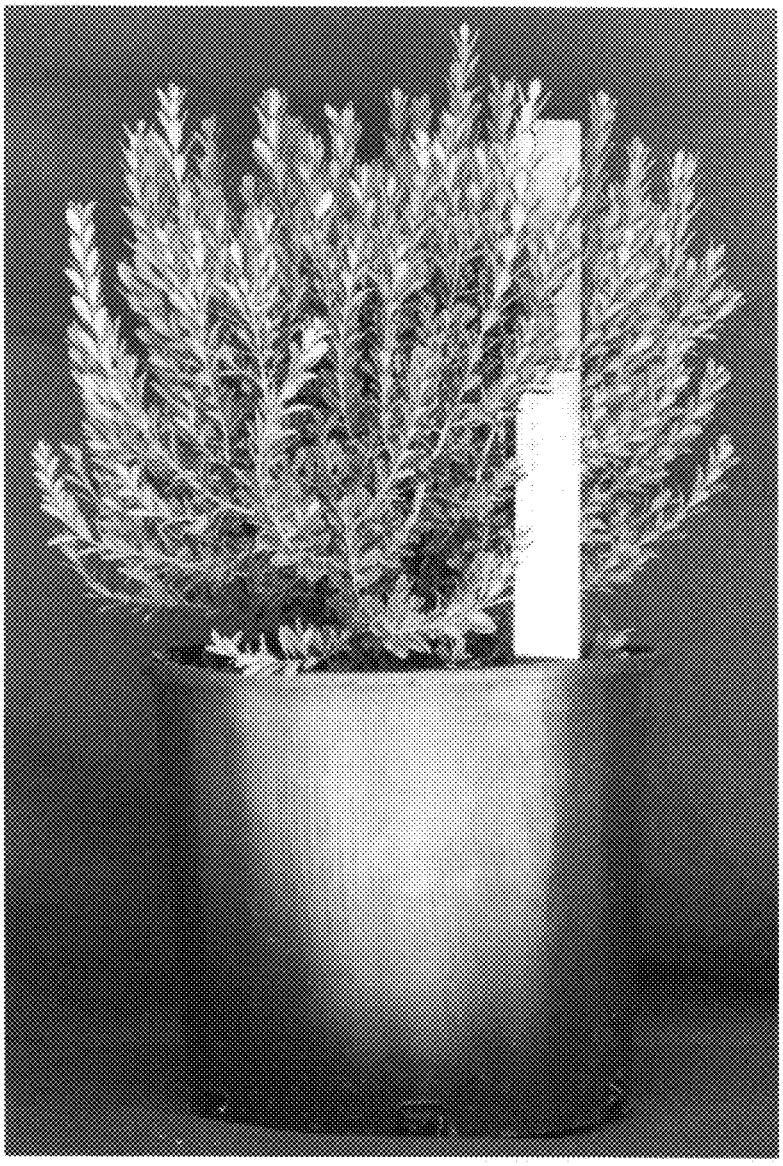
Figure 2:
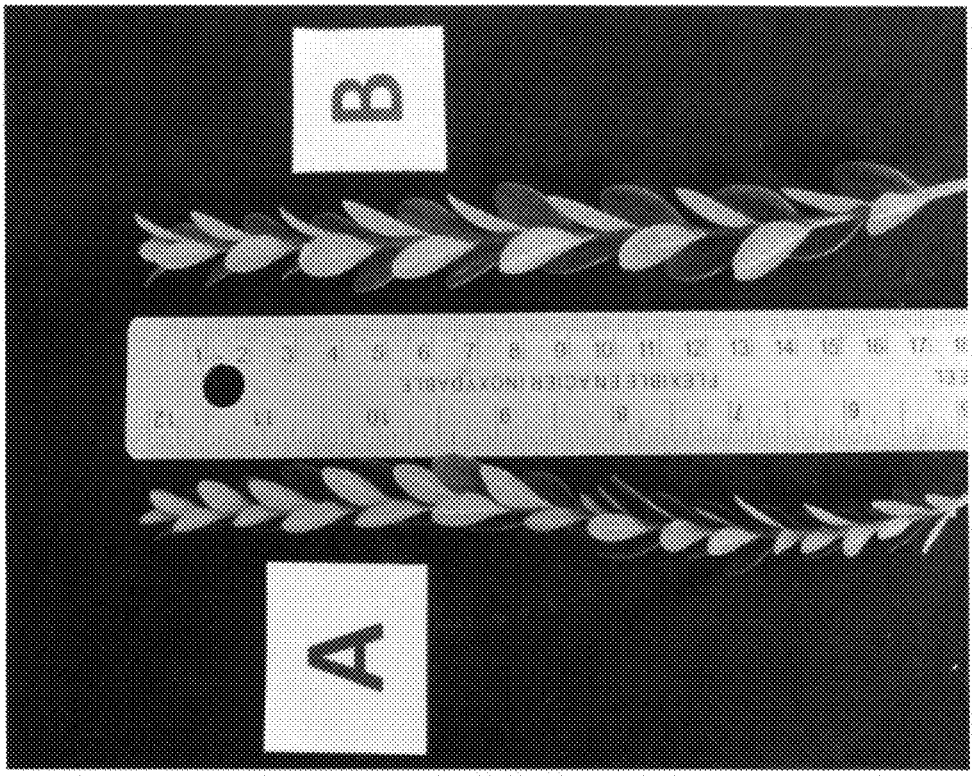

The photograph in FIG. 2 provides a comparison between a branch of 'Gregem' on the top (labeled B) and 'Grejade' (labeled A) on the bottom.

Figure 3:
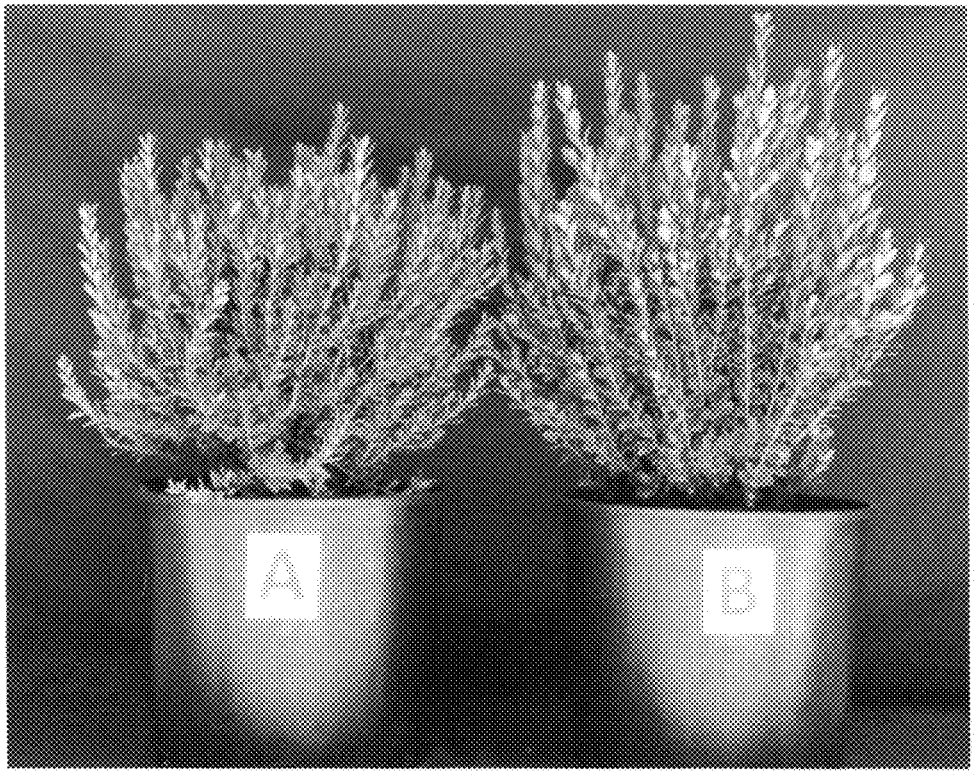

The photograph in FIG. 3 provides a comparison between a plant of 'Grejade' on the left (labeled A) and 'Gregem' (labeled B) on the right.

The colors in the photographs may differ slightly from the color values cited in the detailed botanical description, which accurately describe the colors of the new *Buxus.*

DETAILED BOTANICAL DESCRIPTION

The following is a detailed description of 3 year-old plants of the new cultivar as grown outdoors in three-gallon containers in El Campo, Tex. (main stems pruned once). The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Plant type.*—Evergreen, perennial shrub.
*Plant habit.*—Compact, upright, dense.

*Height and spread.*—Reaches about 30 cm in height with one pruning and 36 cm in height if left un-pruned and spreads to 30 cm in width in a 3-gallon container, mature height in the landscape has not been established to date.

*Cold hardiness.*—At least to U.S.D.A. Zones 5.

*Diseases resistance.*—No susceptibility or resistance has been observed.

*Root description.*—Fibrous.

*Propagation.*—Softwood stem cuttings under mist.

*Growth rate.*—Moderate.

Stem description:

*Shape.*—Round to slightly quadrangular.

*Stem color.*—New growth, 144A; mature bark, 164B with sparse vertical ridges of 143A.

*Stem size.*—Main stems; average of 12 cm in length and 5 mm in width, lateral branches; average of 20 cm in length and 1.5 mm in diameter (at mid point).

*Stem surface.*—New growth; smooth and glabrous, mature growth; rugose, bark-like.

*Branching.*—An average of 4 main stems, an average of 8 main lateral branches emerging from main stems and an average of 6 lateral branches emerging from the main lateral branches.

Foliage description:

*Leaf shape.*—Elliptic.

*Leaf division.*—Simple.

*Leaf base.*—Cuneate.

*Leaf apex.*—Obtuse.

*Leaf fragrance.*—None.

*Leaf venation.*—Pinnate, midrib is conspicuous on lower surface only (145D in color), matches leaf color on upper surface.

*Leaf margins.*—Entire.

*Leaf arrangement.*—Opposite.

*Leaf attachment.*—Sessile.

*Leaf internode length.*—Average of 6 mm in length.

*Leaf surface.*—Glabrous and satiny on upper and lower surface, coriaceous in texture.

*Leaf size.*—An average of 1.8 cm in length and 0.8 cm in width.

*Leaf quantity.*—Average of 26 on a branch 10 cm in length.

*Leaf color.*—Newly expanded leaves; upper surface 144A and lower surface 144B, mature leaves; upper surface N139A, lower surface 144A.

*Leaf buds.*—Up to 0.7 mm in length and width and 147A in color upper surface, 166B in color.

Inflorescence description: No flowers have been observed on the new cultivar to date.

It is claimed:

1. A new and distinct cultivar of *Buxus* plant named 'Grejade' as herein illustrated and described.

* * * * *